United States Patent [19]
Pandian et al.

[11] Patent Number: 5,888,754
[45] Date of Patent: Mar. 30, 1999

[54] DEVICE AND METHOD OF USE FOR DETECTION OF BACTERIAL LIPOPOLYSACCHARIDES

[75] Inventors: Sithian Pandian, Orleans; Eng Jom Aw, Kanata; David I. Smith, Richmond, all of Canada

[73] Assignee: Kalyx Biosciences Inc., Canada

[21] Appl. No.: 753,245

[22] Filed: Nov. 25, 1996

[51] Int. Cl.[6] ................................................. G01N 33/53
[52] U.S. Cl. .............................. 435/7.92; 435/4; 435/71;
435/7.2; 435/7.32; 435/7.72; 435/287.1;
435/287.2; 436/518; 436/527; 436/531;
436/543; 436/810; 422/56; 422/61
[58] Field of Search .............................. 435/4, 7.92, 7.32,
435/7.1, 7.2, 7.72, 287.1, 287.2, 810; 436/518,
543, 527, 531, 810; 422/61, 56

[56] References Cited

U.S. PATENT DOCUMENTS 4,122,158  10/1978  Schmitt ........................................ 424/27
5,510,242  4/1996  Blais et al. .............................. 435/7.32

OTHER PUBLICATIONS

Goni et al. Immunolog. Invest. 1996. 25(3):177–183.

Frobisher. *Fundamentals of Microbiol.* 8th Ed. 1968. p. 301.

Blais et al. Int. J. Food Microbiol. 1991. 14:43–50.

Wang et al. Int. J. Food Microbiol. 1995. 24: 397–406.

*Primary Examiner*—James C. Housel
*Assistant Examiner*—Jennifer Shaver
*Attorney, Agent, or Firm*—Sterne, Kessler, Goldstein & Fox P.L.L.C.

[57] ABSTRACT

This invention relates to a device comprising a hydrophobic solid support coated with a chemical that can capture bacterial lipopolysaccharides (LPS). This invention also relates to the use of such a device in an immunoassay for the detection of microorganisms. This invention also relates to the incorporation of such a device into a diagnostic kit.

12 Claims, 3 Drawing Sheets

Figure 1. Detection of *E.coli* With Bacitracin Coated Cloth Sheet
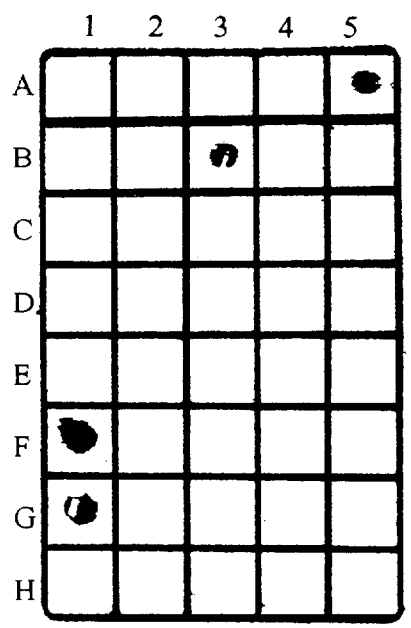
Bacitracin
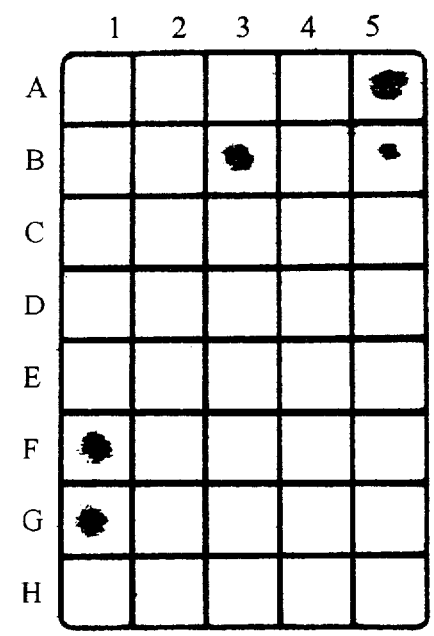
Anti-E. coli Antibody Figure 2. Detection of *Salmonella* with Bacitracin Coated Cloth Sheet Bacitracin Anti-*Salmonella* Antibody

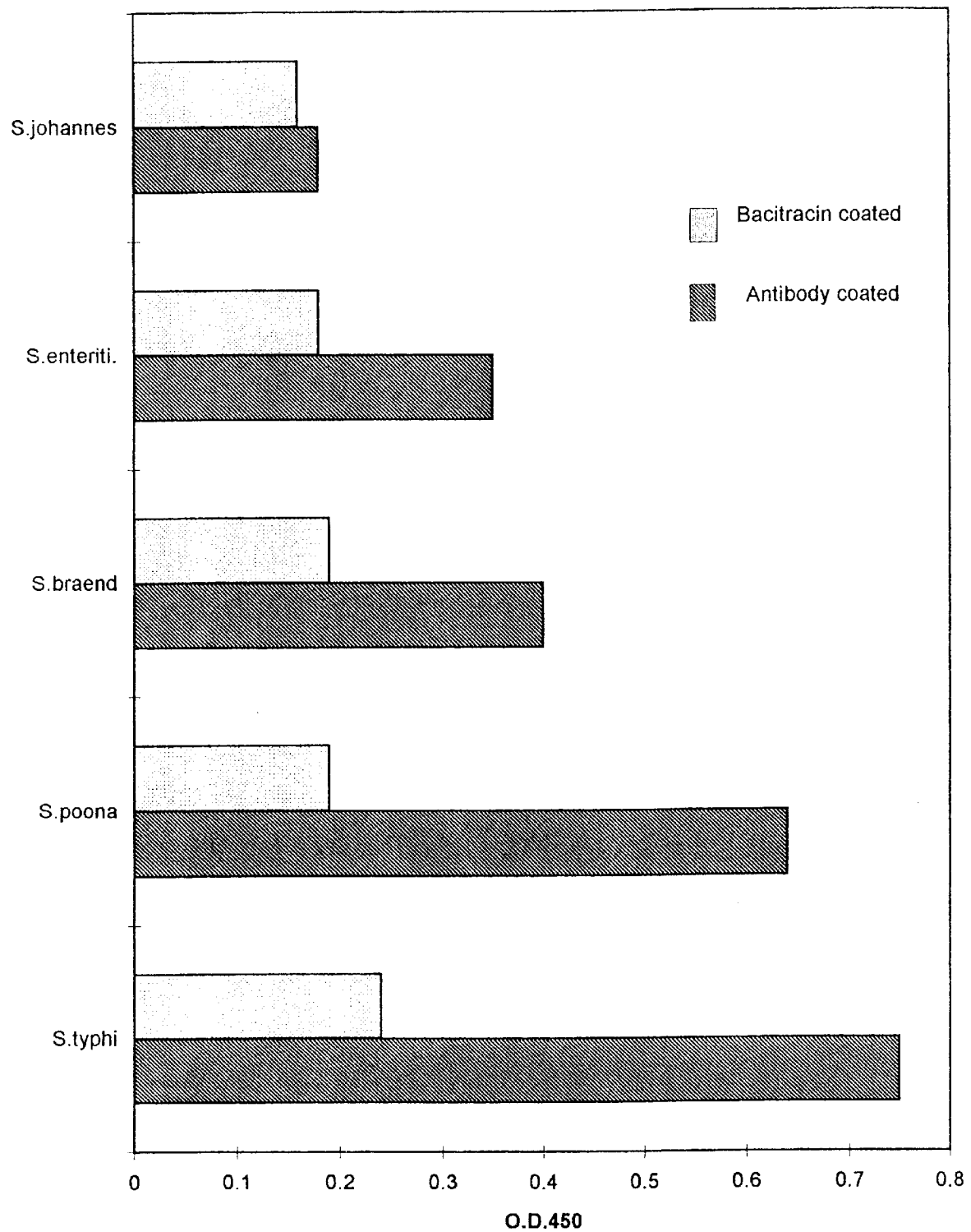
Fig. 3 Detection of Salmonella in microtiter plate ELISA

DEVICE AND METHOD OF USE FOR DETECTION OF BACTERIAL LIPOPOLYSACCHARIDES

BACKGROUND

Rapid diagnostic kits for the detection of microbial antigens constitute an important tool in the world economy. Some of the major developments with these kits have focussed on inventions that offer a shorter assay time, ease of use, minimal or no requirement for sophisticated equipment, low cost, and versatility for testing both small and large number of samples.

One such assay is an Enzyme Linked Immunosorbent Assay (ELISA). In a classical model of ELISA, specific antibody is coated on a solid phase. This antibody is typically referred to as the 'capture antibody'. A test sample containing an antigen is complimentary to the specific antibody is added to the solid phase allowing the antigen to be specifically captured by the antibody immobilized on the solid phase. The non-specific substances in a sample are then removed by simple washing with buffer solutions, Subsequently, an antibody-enzyme conjugate is added which binds to the antigen, or some part of the antigen/antibody complex. After washing away the excess unbound conjugates, an appropriate substrate solution is added so that a colored product (or some other detectable product) is generated and in amounts directly proportional to the antigen present in the test sample. This procedure is well established and well know to those skilled in the art.

The prior art describes a number of solid phases that are coated with a specific antibody in order to capture the antigen in a given test sample. Typically, in order to be able capture the entire amount of the antigen contained in a test sample, a reasonable excess of the antibody has to be coated on the solid phase. For commercial purposes, both polyclonal and monoclonal antibodies are therefore required to be produced in large quantities. Both types of antibodies are relatively expensive to produce. Hence, when large, excess amounts have to be used for coating the solid phase, the cost of the antibody significantly boosts the overall cost of any resulting diagnostic kit or assay. An alternative substance to a 'capture' antibody would therefore be a technological innovation and a commercial attraction. There is therefore a need to find a cheaper way to achieve the same type of binding properties as exhibited by such 'capture' antibodies.

Traditional solid support used for performing ELISA have been, predominantly polystyrene surfaces such as microtiter plates or test tubes, polyethylene or polycarbonate and nylon, or nitrocellulose membranes. More recently, a hydrophobic synthetic polyester cloth sheet has been utilized as the solid phase. The advantages of such a solid support sheet over the other traditional solid supports has been described elsewhere (B. Blais and H. Yamazaki, Use of a hydrophobic cloth for enzyme immunoassay, *Biotechnology Techniques*, 3: 23–26, 1989).

SUMMARY OF THE INVENTION

All Gram negative bacteria possess in their outer membrane a structural entity known to those skilled in the art as lipopolysaccharide (LPS). The LPS consists of three distinct regions: i) a hydrophobic, Lipid-A region, ii) a Core-R oligosaccharide region and iii) a hydrophillic O-polysaccharide side chain. The present invention surprisingly discovered that: (a) the Lipid-A moiety of all Gram negative bacteria can bind strongly to a commonly available antibiotic called acitracin, and (b) bacitracin can bind strongly to most hydrophobic solid supports.

The cloth sheets are first coated with bacitracin as a broad specific capture agent. The bacterial test sample is treated with a detergent solution for exposing their LPS. The resulting treated test sample is then spotted on the bacitracin coated cloth sheet for specific capture of the LPS antigens. The unbound materials are washed away and then an enzyme conjugated antibody (the detector antibody) specific against a given organism or some part of it is added to the coated cloth sheet. After washing away the excess conjugate, the appropriate substrate solution is added in order to generate a detectable product which is indicative of the presence of the target bacterium in the original test sample.

A general embodiment of the present invention involves a device used for the immunoassay of lipopolysaccharides comprising a hydrophobic solid support coated with bacitracin.

A further embodiment of the present invention involves the use of a device for the immunoassay of lipopolysaccharides comprising a hydrophobic solid support coated with bacitracin comprising the steps of (a) prepaying test sample to extract target lipopolysaccharides; (b) applying resulting test sample to bacitracin coated solid support; (c) detection of lipopolysaccharides and/or other parts of said target bound to bacitracin coated solid support.

It is a further embodiment of this invention, to use the biochemical, bacitracin, to coat a solid support to overcome the need to coat said support with a capture antibody.

A further embodiment of the present invention involves a device used for the immunoassay of lipopolysaccharides comprising a hydrophobic solid support coated with a chemical that exhibits bacitracin-like binding properties to lipopolysaccharides.

Yet a further embodiment of the present invention involves a device used for the immunoassay of lipopolysaccharides comprising a hydrophobic solid support coated with a chemical that exhibits bacitracin-like binding properties to lipopolysaccharides.

A further embodiment of this invention relates to a diagnostic kit comprising, in separate packaging: (a) a hydrophobic solid support coated with bacitracin; (b) at least one kit component selected from the group consisting of: (i) a detectably labelled, water soluble antibody specific to LPS or LPS that bas adhered to bacitracin, and (ii) an antibody for LPS or LPS that has adhered to bacitracin, with said antibody being insolubilized, or capable of being insolubilized. It is therefore a general embodiment of this invention to describe a device, and the use of such a device, to achieve a rapid and economical detection of Gram-negative bacteria, particularly, the pathogenic bacteria Salmonella and *E.coli*.

It is yet another embodiment of this invention, to show that the use of bacitracin can allow for that low concentrations of target bacterial LPS to be present, yet still be detected.

It is yet a further embodiment of this invention to describe a device and method of use that allows to overcome the cost associated with using captured antibodies.

It is yet a further embodiment of this invention to describe a device and method of use that allows for easy detection of target bacterial LPS that is not affected by other bacterial or test sample adjuncts.

A BRIEF DESCRIPTION OF THE DRAWINGS

FIG. 1 Results of lipopolysaccharide-antibody assay for the detection of *E. Coli* lipopolysaccharides using a Bacitracin coated hydrophobic synthetic polyester cloth.

FIG. 2 Results of lipopolysaccharide-antibody assay for the detection of Salmonella lipopolysaccharides using a Bacitracin coated hydrophobic synthetic polyester cloth.

FIG. 3 Comparative study for the detection of various strains of Salmonella lipopolysaccharides using microtiter plates/ELISA, said microtiter wells coated with either Bacitracin or monoclonal anti-Salmonella antibody.

DETAILED DESCRIPTION OF THE INVENTION

The advantages in this device and method of use are manifold. Bacitracin being an inexpensive material, when used as a substitute for the capture antibody, immediately contributes to the reduction in the cost of any resulting diagnostic kit. Moreover, antibodies in general have to be quality control tested following each production batch since each batch of the antibody is typically produced in a different animal that may possibly generate antibodies with different biological properties such as affinity and avidity. But since bacitracin is a chemical compound, the variations such as those described above will not be the factors affecting the assay.

The term "cloth sheets" means a hydrophobic synthetic polyester cloth, similar or identical to that described in U.S. Pat. Nos. 5,169,575 and 5,122,452 (herein incorporated by reference).

The term "bacitracin" means a cyclic polypeptide compound naturally synthesized by the bacteria *Bacillus subtilis* and *B. licheniformis* (as further described in Goodmand and Gilman's *The Pharmacological Basis of Therapeutics-8th Edition*, incorporated herein by reference).

The term "bacitracin-like" means a biochemical that exhibits similar or identical binding properties to bacitracin with respect to its ability to bind to a solid support and LPS.

The following is a description of the steps involved in the device and its method of use.

Coating of the Hydrophobic Synthetic Polyester Cloth with Bacitracin

Bacitracin (Sigma Cat. No. B5150) is dissolved in phosphate buffered saline (PBS; 10 mM sodium phosphate buffer, pH 7.2, containing 0.85% sodium chloride) at a concentration of 2.5 mg/ml. Six ml of this solution are poured over a grided hydrophobic synthetic polyester cloth sheet (2"×3"; Kalyx Biosciences, Cat. No. PMU 2101), placed in a suitable incubator tray and incubated at 37° C. for 12–16 hr. Variations include multiple sheets coated in a suitable large box, using 6 ml of die bacitracin solution per sheet. The cloth sheets are then washed with about 30–50 ml of PBST (PBS containing 0.05% Tween-20). The washings can be done by simply holding the sheet in hand and pouring the buffer solution on said cloth sheets and then dried over paper towels. The washings can also be done using a filter-funnel (Immersion Filter, Bel-Art Products, Cat No. F13671-0000). The blocking step, necessary for performing ELISA in traditional protocols is not required Preparation and Application of the Sample One ml of a saturated, overnight culture (approximately, $10^9$ c.f.u./ml) is mixed well with 0.1 ml of a sodium cholate solution (0.75% aq.) and then incubated in a boiling water bath for 10 min. in order to extract the bacterial LPS. The sample is spotted on to the cloth sheet coated with bacitracin. This bacterial LPS sample (2–5 µl) is then spotted onto the cloth and incubated at room temperature for 10 min. The unbound (non-LPS) material in the test sample is washed away with about 30–50 ml of PBST in a manner as described above.

Detection of the LPS Antigen

The LPS of each species of the bacteria can be chemically and therefore antigenically distinct entity. Even though bacitracin appears to be capable of capturing all Gram negative bacterial LPS molecules non-specifically, the detection step of the ELISA, requires an antibody which is highly specific for some parts of the target bacterium. Commercial antibodies of such specificities are available. Indeed, several of these antibodies are commercially available in the form of enzyme conjugates or with a variety of other labels. Six ml of the antibody-enzyme conjugate, diluted in the dilution buffer (PBST-B; PBST containing sufficient blocking agents), are added and incubated at room temperature for 10 min. The excess unreacted conjugate is washed away and then 6 ml of the substrate solution are added to the cloth sheet and incubated until the colored spots appear (typically in about 10 min.). The reaction is stopped by washing the sheet with deionized water.

The following examples are included by way of illustration and are by no means limiting to the application of he invention.

EXAMPLE 1

Detection of *E.coli* 0157: H7 with bacitracin coated cloth sheet ELISA.

*E.coli* 0157: H7 and other bacteria listed in Table 1 were grown to saturation and their LPS were extracted by boiling 1 ml of the bacterial culture with 0.1 ml of sodium cholate (0.75% in PBS) solution for 10 min. Three µl samples were spotted on the bacitracin coated cloth sheet and incubated at room temperature for 10 min. In a control set of tests, the samples were spotted on cloth sheet coated with an anti-*E.coli* 0157 antibody. After washing the sheets with PBST, six ml of anti-*E.coli* 0157: H7 -HRP conjugate (Kirkegaard & Perry Laboratories, Cat No. 04-05-90; diluted 4000 times with the Kalyx Universal dilution buffer, Kalyx Cat. No. PMU 2405) were added and incubated at room temperature for 10 min. The excess unbound conjugate was washed as previously described and six ml of the substrate (TMB Membrane Peroxidase substrate; Kirkegaard & Perry Laboratories) were added to the sheets. The colored spots appeared corresponding to the positive sample spots within 10 min. The reaction was stopped by washing the cloth sheets with deionized water.

The results are shown in FIG. 1. It can be seen that the bacitracin coating of the cloth is as efficient in capturing the LPS antigens as is the specific antibody. The intensities of the signals are comparable.

The results summarized in Table 1 indicate that this detection method is highly target specific and that it does not respond to other bacteria except some members of Group N Salmonella (e.g. *S. urbana*) which shares the same LPS antigenic determinant as that of *E.coli* 0157 (E.C.D. Todd et al. Rapid hydrophobic grid membrane filter-enzyme labeled antibody procedure for identification and enumeration of *E.coli* 0157 in foods. Applied and Environmental Microbiology, 54: 2536–2540, 1988).

The results are depicted in FIG. 3 and indicate that even though the bacitracin coated wells are capable of detecting the Salmonella strains reasonable well, the antibody coated wells are of much higher efficiency. In this respect, the microtiter plates behave slightly differently than the cloth sheets.

EXAMPLE 2

Minimal detection level of *E. coli* 0157: H7 with bacitracin coated cloth sheet.

*E.coli* and other bacteria listed in Table 1 were tested. Into sterile enrichment medium (TSY; Trypticase Soy broth containing 0.6% yeast extract) were inoculated 0, 10, 50, 100 or 500 c.f.u. of *E. coli* 0157: H7 bacteria either as pure inoculum or in the presence of a fairly heavy inoculum load of contaminating bacteria that are phylogenetically related to *E.coli.* 0157: H7. The inocula were allowed to grow at 37° C. for 12 to 16 hr. (overnight). Their LPS were extracted by boiling 1 ml of the bacterial culture with 0.1 ml of sodium cholate (0.75% aq) solution for 10 min. Three μl samples were spotted on the bacitracin coated cloth sheet and incubated at room temperature for 10 min. After washing the cloth sheet with PBST, six ml of anti-*E.coli* 0157: H7 -HRP conjugate (Kirkegaard & Perry Laboratories, Cat No. 04-05-90; diluted 4000 times with the Kalyx Universal dilution buffer, Kalyx Cat. No. PMU 2405) were added and incubated at root temperature for 10 min. The excess unbound conjugate was washed as before and six ml of the substrate were added to the sheet, Normally, the colored spots appeared corresponding to the positive sample spots within 10 min. The reaction was stopped by washing the cloth sheet with deionized water.

The results are shown in Table 2 and indicate that the assay is able to specifically detect at least 10 c.f.u of *E.coli* 0157 cells following pre-enrichment. The results also confirm that the assay is specific to the detection of *E.coli.* 0157 and does not respond to even closely related bacteria. Finally, it appears that the presence of the LUS of such contaminating bacteria in the test samples does not interfere with the efficiency of the assay.

EXAMPLE 3
Detection of *E.coli* inoculated into ground beef with bacitracin coated cloth sheet.

Ground beef samples were obtained from local retailers. Twenty five gram samples of beef were homogenized with 225 ml of sterile enrichment medium (TSY; Trypticase Soy broth containing 0.6% yeast extract) and into this was inoculated 0, 10, 50, 100 or 500 c.f.u. of *E. coli* 0157: H7 bacteria. The inocula were allowed to grow at 37° C. for 12 to 16 hr., or overnight. LPS antigens were extracted from these cultures as described in Example 1 and their assayed using bacitracin coated cloth sheet. The results of the assay appear in Table 3 and indicate that this assay can detect at least 10 cells of *E.coli* inoculated in ground beef following pre-enrichment. The results further indicate that presence of food materials do not in any way interfere with the assay.

EXAMPLE 4
Detection of *E.coli* inoculated into ground beef along with low and high levels of contaminating bacteria.

The experimental design was the same as described in Example 2 with the exception that *E.coli* was inoculated along with phylogenetically related bacteria and other food associated bacteria at different c.f.u per inoculum. The results of the assay appear in Table 4 and confirm that the assay's sensitivity is not altered by the presence of high levels of contaminating bacteria, even of bacteria closely related to *E.coli*.

EXAMPLE 5
Specific detection of Salmonella with bacitracin coated cloth sheet.

Salmonella and other bacteria listed in Table 5 were grown to saturation and their LPS were extracted by boiling 1 ml of the bacterial culture with 0.1 ml of sodium cholate (0.75%) solution for 10 min. Two μl samples were spotted on the bacitracin coated cloth sheet and incubated at room temperature for 10 min. In a control set of tests, the samples were spotted on a cloth sheet coated with a rabbit anti-Salmonella antibody. After washing the sheets with PBST, 6 ml of a mouse monoclonal anti-Salmonella antibody were added and incubated at room temperature for 10 min. The excess unbound antibody was washed as described above. Six ml of anti-mouse IgG-HRP conjugate (Rockland, diluted 10,000 times in Kalyx Universal dilution buffer) and incubated room temperature for 10 min. After washing the sheets as described above, 6 ml of TMB substrate were added to the sheets. Normally, the colored spots appeared corresponding to the positive sample spots within 10 min. The reaction was stopped by washing the cloth sheets with deionized water.

The results are shown in FIG. 2. It can be seen that the bacitracin coating of the cloth is as efficient in capturing the LPS antigens of all the Salmonella as is the specific antibody. The intensities of the signals are comparable, and spectrum of specificity of the assay are also comparable.

EXAMPLE 6
Stability of bacitracin coated on cloth sheet.

The cloth sheet was coated with bacitracin (2.5 mg/ml of PBS) as per the standard protocols, and then stored dry or wetted with PBS, at 37° C., room temperature or 4° C. At periodic intervals, the cloth sheets are withdrawn and used in the assay for the detection of Salmonella as per the method given in Example 5. The results are given Table 6, and indicate that Bacitracin coated cloth sheets retain their capacity to bind LPS even after 1 month of a storing at 4° C. or at least two weeks at 37° C.

EXAMPLE 7
Use of bacitracin coated microliter plates in ELISA: Detection of Salmonella.

Microtiter plates were coated with bacitracin at a concentration of 2.5 mg/ml of PBS or coated with an appropriate concentration of anti-Salmonella antibody (in PBS). The coating was done with 100 μl of solution per each well (Immulon IV, Dynatech), followed by incubation at 37° C. overnight. The wells were washed three tones with PBST, and blocked with 100 μl per well of Kalyx Universal Blocking buffer (Cat.No.PMU 2104) for 1 hr at room temperature. The wells were washed as described above and 100 μl of the LPS extracts of the bacteria listed in FIG. 3 were added to the wells and incubated at room temperature for 30 min., then washed three times with PBST. One hundred μl of a dilute solution of the anti-Salmonella was added, incubated for 30 min., washed with PBST and 100 μl of anti mouse IgG-HRP conjugate (diluted in Kalyx Universal dilution buffer) were added to the wells, incubated at room temperature for 30 min. and washed three times with PBST. The TMB microwell substrate solution (100 μl; KPL Cat.No. 50-76-05) was added and incubated at room temperature until sufficient blue color developed. The reaction was stopped by the addition of 50 μl of 0.1M sulfuric acid and the optical density of the resulting yellow color was measured at 405 nm. in an ELISA-reader (Bio-Tek instruments).

The results indicate that bacitracin can function at least as efficiently as the capture antibody and therefore can be used in ELISA in place of the capture antibody.

1. Detection of *E. coli* 0157:H7 with bacitracin coated cloth sheet.

| Bacterial Sample | Test Results (positive/No. times tested) |
| --- | --- |
| *Escherichia coli*[a] | 0/6 |
| *Escherichia coli* 011:NM | 0/4 |
| *Escherichia coli* 05:NM | 0/4 |
| *Escherichia coli* 026:H11 | 0/5 |
| *Escherichia coli* 0157:H12 | 6/6 |
| *Escherichia coli* 0157:H7 | 6/6 |
| *Escherichia coli* 0157:H7 | 6/6 |

-continued

1. Detection of *E. coli* 0157:H7 with bacitracin coated cloth sheet.

| Bacterial Sample | Test Results (positive/No. times tested) |
|---|---|
| (ATCC 35150; Reference strain) | |
| *Escherichia hermanii* | 0/2 |
| *Bacillus cereus* | 0/3 |
| *Pseudomonas aeruginosa* | 0/2 |
| *Yersinia enterocolitica** | 0/2 |
| *Yersinia enterocolitica* 0:9 | 0/4 |
| *Yersinia intermedia* | 0/2 |
| *Enterococcus faecalis* | 0/2 |
| *Shigella sonnei* | 0/2 |
| *Enterobacter cloacae* | 0/4 |
| *Salmonella typhimurium* | 0/3 |
| *Salmonella urbana*[a] | 6/7 |
| *Listeria innocua* | 0/4 |
| *Listeria ivanovii* | 0/4 |
| *Listeria welshimeri* | 0/2 |
| *Klebsiella pneumoniae* | 0/2 |
| *Citrobacter freundii* | 0/2 |
| *Proteus vulgaris* | 0/2 |

*unknown serotype
[a]shares same epitope as LPS antigen of *E. coli* 0157:H7

TABLE 2

Sensitivity of *E. coli* 0157:H7 Detection in bacterial cultures with and without contaminating bacteria using bacitracin coated cloth sheet.

| CFU or *E. coli* 0157:H7 | Contaminating Bacteria[a] | Test Result |
|---|---|---|
| 0 | none | − |
| 1 | none | − |
| 10 | none | + |
| 50 | none | + |
| 100 | none | + |
| 1000 | none | + |
| 0 | *E. coli* 05: NM, *E. cloacae* | − |
| 1 | *E. coli* 05: NM, *E. cloacae* | − |
| 10 | *E. coli* 05: NM, *E. cloacae* | + |
| 50 | *E. coli* 05: NM, *E. cloacae* | + |
| 100 | *E. coli* 05: NM, *E. cloacae* | + |
| 1000 | *E. coli* 05: NM, *E. cloacae* | + |
| 0 | *E. coli* 05: NM | − |
| 0 | *E. cloacae* | − |
| 0 | *E. coli* 026: H11 | − |

[a]100 cells inoculated of each bacteria

TABLE 3

Sensitivity of detection of *E. coli* 0157:H7 in ground beef using bacitracin coated cloth sheet.

| CFU of *E. coli* 0157:H7 | Contaminating Bacteria[a] | Test Result |
|---|---|---|
| 0 | none | − |
| 10 | none | + |
| 50 | none | + |
| 100 | none | + |
| 500 | none | + |

TABLE 4

Sensitivity of *E. coli* 0157:H7 in ground beef in presence of contaminating bacteria using bacitracin coated cloth sheet

| CFU of *E. coli* 0157:H7 | Contaminating Bacteria[a] | Test Result |
|---|---|---|
| 0 | *E. coli* 05: NM, *E. cloacae* | − |
| 10 | *E. coli* 05: NM, *E. cloacae* | + |
| 50 | *E. coli* 05: NM, *E. cloacae* | + |
| 100 | *E. coli* 05: NM, *E. cloacae* | + |
| 500 | *E. coli* 05: NM, *E. cloacae* | + |
| 0 | *L. innocua, L. ivanovii* | − |
| 10 | *L. innocua, L. ivanovii* | − |
| 50 | *L. innocua, L. ivanovii* | + |
| 100 | *L. Innocua, L. ivanovii* | + |
| 500 | *L. innocua, L. ivanovii* | + |

[a]100 cells inoculated of each bacteria

TABLE 5

Specific detection of Salmonella using bacitracin coated cloth sheet; Pure culture LPS extracts tested.

| Bacterial Sample | Test Results Positive/No. times tested |
|---|---|
| *Salmonella typhimurium* | 61/61 |
| *S. cerro* | 61/61 |
| *S. poona* | 61/61 |
| *S. braenderup* | 61/61 |
| *S. anatum* | 61/61 |
| *S. enteritidis* | 61/61 |
| *S. minnesota* | 61/61 |
| *S. johannesburg* | 61/61 |
| *S. rubislaw* | 61/61 |
| *Shigella sonnei* | 0/61 |
| *E. coli* | 0/61 |
| *Pseudomonas aeruginosa* | 0/61 |
| *Citrobacter freundii* | 0/61 |
| *Enterobacter cloacae* | 0/61 |

TABLE 6

Stability of bacitracin coated cloth sheets using bacitracin coated cloth sheet: ELISA for Salmonella.

| No. of weeks | 37° C. dry | 37° C. wet | Room temperature dry | Room temperature wet | 4° C. dry | 4° C. wet |
|---|---|---|---|---|---|---|
| 1 | ++++ | ++++ | ++++ | ++++ | ++++ | ++++ |
| 2 | ++++ | ++++ | ++++ | ++++ | ++++ | ++++ |
| 3 | nt | nt | ++++ | ++++ | ++++ | ++++ |
| 4 | | | ++++ | ++++ | ++++ | ++++ |

++++ Activity same as Control (fleshly coated sheet)
+++ 75% of the control activity
++ 50% of the control activity
+ 25% of the control activity
− No activity
nt Not tested

We claim:

1. A device for detecting lipopolysaccharides of target Gram negative bacteria, said device consisting of a hydrophobic solid support having bacitracin adsorbed strongly thereon in a manner that enables said bacitracin to function as a broad specific capture agent for Gram negative bacterial lipopolysaccharides.

2. A device according to claim 1, wherein said lipopolysaccharides are present on the cell walls of said Gram negative bacteria.

3. A device according to claim 1, wherein said hydrophobic solid support is selected from the group consisting of:
   (a) a synthetic polyester cloth; and
   (b) a polystyrene microtitre plate.

4. A device according to claim 1, wherein said hydrophobic solid support is selected from the group consisting of:

(a) a polystyrene test tube;
(b) a polyethylene membrane;
(c) a polycarbonate membrane;
(d) a nylon membrane; and
(e) a nitrocellulose membrane.

5. A method for detection of Gram negative bacterial lipopolysaccharide in a test sample comprising the steps of:
   (a) treating a test sample to extract target lipopolysaccharides;
   (b) applying said target lipopolysaccharide extract to a device comprising a hydrophobic solid support having bacitracin adsorbed to said support as a broad specific capture agent for lipopolysaccharides, wherein said target lipopolysaccharide extract binds to said bacitracin-coated surface;
   (c) washing said device; and
   (d) detecting the presence of said target lipopolysaccharide extract bound to said bacitracin-coated surface by an assay.

6. A method according to claim 5, wherein in step (b), said hydrophobic solid support is selected from the group consisting of:
   (a) a synthetic polyester cloth; and
   (b) a polystyrene microtitre plate.

7. A method according to claim 5, wherein in step (b), said hydrophobic solid support is selected from the group consisting of:
   (a) a polystyrene test tube;
   (b) a polyethylene membrane;
   (c) a polycarbonate membrane;
   (d) a nylon membrane; and
   (e) a nitrocellulose membrane.

8. A method according to claim 5, wherein said lipopolysaccharides are present on the cell walls of said Gram negative bacteria.

9. A diagnostic test kit comprising:
   (a) a hydrophobic solid support having bacitracin adsorbed to said support in a manner that enables said bacitracin to function as a broad specific capture agent for Gram negative bacterial lipopolysaccharides;
   (b) at least one reagent selected from the group consisting of:
      (i) water-soluble antibody, said antibody being capable of specific binding to lipopolysaccharide or to an epitope of a lipopolysaccharide that has adhered to bacitracin, said antibody being labeled to permit subsequent detection; and
      (ii) an antibody that is capable of being insolubilized and subsequently detected; said antibody being capable of specific binding to lipopolysaccharide or to an epitope of a lipopolysaccharide that has adhered to bacitracin; and
   (c) instructions for use of the test kit.

10. A diagnostic test kit according to claim 9, wherein said hydrophobic solid support is selected from the group consisting of:
    (a) a synthetic polyester cloth; and
    (b) a polystyrene microtitre plate.

11. A diagnostic test kit according to claim 9, wherein said hydrophobic solid support is selected from the group consisting of:
    (a) a polystyrene test tube;
    (b) a polyethylene membrane;
    (c) a polycarbonate membrane;
    (d) a nylon membrane; and
    (e) a nitrocellulose membrane.

12. A diagnostic test kit according to claim 9, wherein detection of said Gram negative bacterial lipopolysaccharides is unaffected by bacterial or test sample adjuncts.

* * * * *